United States Patent [19]

Schwager

[11] Patent Number: 5,706,826
[45] Date of Patent: Jan. 13, 1998

[54] GUIDE WIRE WITH HELICAL COIL

[75] Inventor: Michael Schwager, Winterthur, Switzerland

[73] Assignee: Schneider (Europe) A.G., Bulach, Switzerland

[21] Appl. No.: 576,242

[22] Filed: Dec. 21, 1995

[30] Foreign Application Priority Data

Mar. 2, 1995 [EP] European Pat. Off. .............. 95103006

[51] Int. Cl.$^6$ ...................................................... A61B 5/00
[52] U.S. Cl. .................. 128/772; 604/95; 604/96; 604/280; 604/281
[58] Field of Search ..................... 128/772, 657, 128/658; 604/95–96, 280–283, 164

[56] References Cited

U.S. PATENT DOCUMENTS

| Re. 33,911 | 5/1992 | Samson et al. | 128/772 |
|---|---|---|---|
| 4,538,622 | 9/1985 | Samson et al. | 128/772 |
| 4,545,390 | 10/1985 | Leary | 128/772 |
| 4,554,929 | 11/1985 | Samson et al. | 128/772 |
| 4,721,117 | 1/1988 | Mar et al. | 128/772 |
| 4,748,986 | 6/1988 | Morrison et al. | 128/772 |
| 4,763,647 | 8/1988 | Gambale | 128/657 |
| 4,922,924 | 5/1990 | Gambale et al. | 128/772 |
| 5,063,935 | 11/1991 | Gambale | 128/657 |
| 5,067,489 | 11/1991 | Lind | 128/772 |
| 5,143,085 | 9/1992 | Wilson | 128/772 |
| 5,144,959 | 9/1992 | Gambale et al. | 128/772 |
| 5,147,317 | 9/1992 | Shank et al. | 604/164 |
| 5,174,302 | 12/1992 | Palmer | 128/772 |
| 5,259,393 | 11/1993 | Corso, Jr. et al. | 128/772 |
| 5,333,620 | 8/1994 | Moutatis et al. | 128/772 |
| 5,345,945 | 9/1994 | Hodgson et al. | 128/772 |
| 5,421,348 | 6/1995 | Larnard | 128/772 |
| 5,429,139 | 7/1995 | Sauter | 128/772 |

FOREIGN PATENT DOCUMENTS

| 0318046 | 5/1989 | European Pat. Off. . |
|---|---|---|
| 0405823A3 | 1/1991 | European Pat. Off. . |
| 0419277 | 3/1991 | European Pat. Off. . |
| 0625358 | 11/1994 | European Pat. Off. . |
| 9005486 | 5/1990 | WIPO . |
| 9204072 | 3/1992 | WIPO . |
| 9214508 | 9/1992 | WIPO . |
| 9219151 | 11/1992 | WIPO . |
| 9406347 | 3/1994 | WIPO . |
| 9524237 | 9/1995 | WIPO . |

OTHER PUBLICATIONS

United States Patent Application Serial No. 08/295,976, filed Aug. 25, 1994, commonly owned by assignee of above–captioned application.

United States Patent Application Serial No. 08/581,416 filed Dec. 29, 1995, commonly owned by assignee of above–captioned application.

United States Patent Application Serial No. 08/581,098, filed Dec. 29, 1995, commonly owned by assignee of above–captioned application.

*Primary Examiner*—Max Hindenburg
*Assistant Examiner*—Pamela L. Wingood
*Attorney, Agent, or Firm*—Peter C. Richardson; Lawrence C. Akers; Philip C. Strassburger

[57] ABSTRACT

The guide wire comprises an elongated flexible shaft which is tubular. A helical coil assembly of radiopaque material comprises a first coil having a proximal portion threadedly force fitted into the tubular portion of shaft. A second coil has a proximal portion surrounding and threadingly engaging the distal portion of the first coil, and a distal portion terminating into a tip.

18 Claims, 1 Drawing Sheet

GUIDE WIRE WITH HELICAL COIL

BACKGROUND OF THE INVENTION

This invention relates to guide wires comprising an elongated flexible shaft with a proximal portion and a distal portion, and a coaxial helical coil assembly at the distal portion of said shaft, said coaxial helical coil assembly comprising a first coil having a proximal portion and a distal portion, said first coil joined to the shaft, and a second coil having a proximal portion joined to the distal portion of the first coil and a distal portion terminating into a tip.

Guide wires are commonly used, for example for positioning catheters through blood vessels. Typically, a guide catheter may be inserted through the vasculature and the guide wire is inserted into a blood vessel via such guide catheter. A balloon catheter may then be pushed onto the guide wire for proper location into the blood vessel.

Usually, the distal end of the guide wire is shapeable to conform with the tortuous pathways of the blood vessels, and the shaft of the guide wire must have a good kink resistance to assure pushability of the guide wire and torque transmission thereto. A further requirement is that the distal end of the guide wire be radiopaque so that the guide wire may be easily tracked along the vasculature.

European Patent Application N° 93810371.0 describes a guide wire comprising a flexible shaft with a proximal portion and a distal portion. This shaft is provided on its outside, with the exception of its distal portion, with a Teflon® coating to reduce friction of the guide wire when moved within a guide catheter. A flexible helical coil assembly surrounds the distal portion of the shaft. This helical coil assembly has a radiographically visible distal helical coil and a proximal helical coil which is radiographically invisible. The proximal helical coil and the distal helical coil are attached to each other by a connecting helical coil one end of which is screwed into the proximal helical coil and the other end of which is screwed into the distal helical coil. The proximal end of the proximal helical coil is soldered to the shaft and the distal end of the distal helical coil is welded to the distal end of the shaft forming a rounded tip. This configuration allows having different materials for the coiled distal portion of the guide wire with a three coil assembly behaving in its flexibility essentially like a helical coil wound from a single wire.

The document WO 92/19151 shows a catheter guide wire comprising a flexible torqueable proximal wire section which is followed by a more flexible intermediate section and a most flexible distal end section. A wire core in the guide wire is formed of a flexible, torqueable wire filament material such as stainless steel. The segment of the core forming the proximal wire section has a substantially uniform diameter along its length. Within the intermediate section, the core is tapered from the proximal section diameter down to a reduced diameter and the wire core of the intermediate section is covered along its length by a flexible polymer covering the major function of which is to provide a low-friction surface along intermediate section and also to provide column support to the reduced diameter core of the intermediate section to reduce its tendency to buckle under axial compression. Beneath the polymer covering, a radiopaque ribbon of metal is wound around the wire core, and this ribbon coil extends from the tapered segment of the intermediate section to the distal junction of the intermediate section. The distal section of the guide wire is encased in a flexible sleeve made of a soft flexible helical coil which is formed conventionally as a winding of radiopaque wire strand. Attachment of this sleeve to the wire core is made by solder joints, one at the proximal junction of the end section and one at a rounded distal end junction of the end section. According to a variant, a portion of the helical coil ribbon is replaced with an inner wire coil; in this variant, an inner wire coil extends from helical coil ribbon to the proximal junction of the end section which is joined by a solder joint to the wire core. This inner coil thus serves as an anchor point for the distal end of the helical coil ribbon and also as an anchor point for the polymer covering on the intermediate core section.

WO 92/04072 describes a dual coil guide wire with radiopaque distal tip having a shaft formed of a centrally located core wire about which is mounted a single outer helical coil spring. The core wire is longer than the outer helical coil spring, with the helical coil spring and core wire having common distal ends. The spring is brazed at both its distal and proximal ends to the core wire, the distal brazing of the core wire and helical coil spring being rounded. A second small radiopaque helical coil spring is fitted in the distal end of the outer helical coil spring and brazed to the core wire and outer helical coil spring at a location proximal the helical coil spring distal end. In a variant, an outer helical coil spring is brazed at two locations to the inner core wire and the radiopaque core is placed between these two brazing locations and between the helical coil spring and the core wire; the radiopaque coil may or may not be brazed directly to the core wire, preferably, the radiopaque coil is freely moveable between the two brazed locations of the outer helical coil spring to the inner core wire.

U.S. Pat. No. 4,748,986 relates to a floppy guide wire with opaque tip comprising a flexible elongate element which can be in the form of a wire-like hollow cylindrical element or a wire-like cylindrical core. The elongate element is adjoined by an intermediate tapered portion which in turn is adjoined by a distal flattened portion. An elongate coil is coaxially disposed on the flexible elongate element and extends substantially from the proximal end thereof to the commencement of the tapered portion, this coil being tightly wound so that its turns butt each other. A coating of smooth material is provided on the coil. A second elongate coil of radiopaque material is provided to adjoin the first coil. The proximal portion of this second coil is formed with turns that butt each other while the turns at the distal portion thereof are stretched to provide flexibility. The proximal portion of the second coil is threaded into the distal portion of the first elongate coil to form a connection therebetween. Alternatively, the two coils can have these same ends butted together. A safety ribbon is disposed internally of the second coil with its distal end brazed into a rounded protrusion brazed in the distal end of the second coil. The distal extremity of the first elongate coil, the proximal extremity of the second coil, the proximal extremity of the safety ribbon and the tapered portion of the flexible elongate element are bonded into a unitary assembly by a brazing compound.

U.S. Pat. No. 4,922,924 also shows a two coil assembly in which the two coils are screwed into each other with the ends of the bifilar section being welded to each other and to the central shaft. As in the previous guide wire a safety wire connects a rounded tip at the distal extremity of the second coil to the shaft.

U.S. Pat. Nos. 5,063,935 and 5,144,959 both show a guide wire including a shaft having an outer helical coil attached to the distal region of the shaft and terminating in a tip weld this outer coil is formed from a highly radiopaque wire. A smaller diameter inner helical coil formed from a larger diameter highly radiopaque wire is disposed within the outer coil and is attached at its proximal end to the distal end of the shaft and at its distal end to the tip weld.

EP-A1-0318046 describes a medical guide wire consisting of a core having a body portion of a first diameter, a distal portion of a relatively smaller diameter, and a flat distal end disposed in the tip region and spaced proximally from a round tip element that defines the distal end of the guide wire. A first coil is joined to the core body and extends along the core to a termination point in the distal region, proximal of the end of the core. A relatively more flexible second coil made of a radiopaque material is joined at the proximal end to the first coil and joined at its distal end to the round tip element. The first coil and second coil are joined by removing wire material from the outer diameter of the first coil to a depth substantially equal to the diameter or thickness of the wire forming the second coil whereby a smooth flat surface is created on the first coil. The proximal end of the second coil is then disposed over the distal end of the first coil and the two are joined by solder or the like. The assembly is said to result in a joint of substantially uninterrupted flexibility.

It is an object of this invention to improve over the cited art by means of a guide wire which is easy to manufacture and highly versatile while having excellent qualities of pushability and shapeability.

SUMMARY OF THE INVENTION

In sum, the present invention relates to a guide wire comprising an elongated flexible shaft with a proximal portion and a distal portion, and a coaxial helical coil assembly at the distal portion of the shaft. The coaxial helical coil assembly has a first coil with a proximal portion and a distal portion, the first coil joined to the shaft, and a second coil with a proximal portion joined to the distal portion of the first coil and a distal portion terminating into a tip. At least the distal portion of the shaft is tubular. The proximal portion of the first coil is threadedly force fitted into the tubular distal portion of the shaft, whereby the first coil makes a thread way into the tubular distal portion of the shaft. The proximal portion of the first coil may have adjacent windings which are spaced apart. An adhesive may be sucked into the proximal portion of the first coil. The proximal portion of the second coil may surround the distal portion of the first coil, and the proximal portion of the second coil may have windings in threading engagement with windings of the distal portion of the first coil. The proximal portion of the second coil may abut against the distal portion of the shaft. The proximal portion of the second coil may be flush with the distal portion of the shaft. The guide wire may further comprise core means extending through the first coil, which may have a proximal portion in flush engagement with the first coil. The core means may have a proximal end in longitudinal abutment against the proximal end of the first coil, and a distal portion terminating into the tip of the distal portion of the second coil. At least the tubular distal portion of the shaft may be made of an elastic nickel titanium alloy, and at least the tubular distal portion of the shaft may be made of a plastic material. The first and second coils may be made of high density metal, such as tungsten.

Accordingly, the combination of at least the distal portion of the shaft being tubular with the proximal portion of the first coil being threadedly force fitted into said tubular portion of the shaft creates a shape conforming assembly which has the configuration, safety and resistance of a threaded assembly, without the need to specifically machine a thread in the tubular portion of the shaft. As the first coil makes the thread way into the tubular portion of the shaft, the assembly is tolerance free. The shaft is free from any coil coverage which may require coatings of slippery materials and the shaft may be designed at will for best flexibility and kinking resistance, with the easiest choice in varying diameters for flexibility control. The shaft may be tubular only at its distal portion or it may be fully tubular, for instance for use in a pressure measuring equipment.

The proximal portion of the first coil may have adjacent windings which are spaced apart in order to facilitate the threadingly fitting into the tubular portion of the shaft. And this configuration also allows the sucking and full penetration of an adhesive into the proximal portion of the coil, which greatly facilitates the definite locking of the proximal portion of the coil in the distal portion of the shaft.

The proximal portion of the second coil may surround the distal portion of the first coil and the proximal portion of the second coil may have windings in threading engagement with windings of the distal portion of the first coil, which provides a simple, tolerance free assembly between the first and second coils which requires no particular grinding of the first coil. Within this configuration, the proximal portion of the second coil may abut against the distal portion of the shaft, which locks the threading engagement and provides a continuity between the shaft and second coil. Where the proximal portion of the second coil is flush with the distal portion of the shaft, maximal continuity between shaft and coil is achieved without difficulty because the wire size and consequently the diameters of the second coil may be chosen at will, and there is still no need to grind or otherwise machine the distal portion of the first coil.

Core means may extend through the first coil, preferably with a proximal portion in flush engagement into the first coil. This provides a coil support which does not interfere with the shaft.

Where the core means have a proximal end in longitudinal abutment against the proximal end of the first coil and a distal end terminating into the tip of the distal portion of the second coil, a further safety is achieved for the assembly of the two coils which is stress free for the shaft structure and which leaves the shaft structure free of any obstruction proximally of the core assembly, for example for pressure measuring purposes.

DESCRIPTION OF THE DRAWING

These and other objects, features and advantages of the invention will become readily apparent from the following detailed description with reference to the accompanying drawing which shows, diagrammatically and by way of example only a preferred but still illustrative embodiment of the invention.

DESCRIPTION OF PREFERRED EMBODIMENTS

Figure 1:
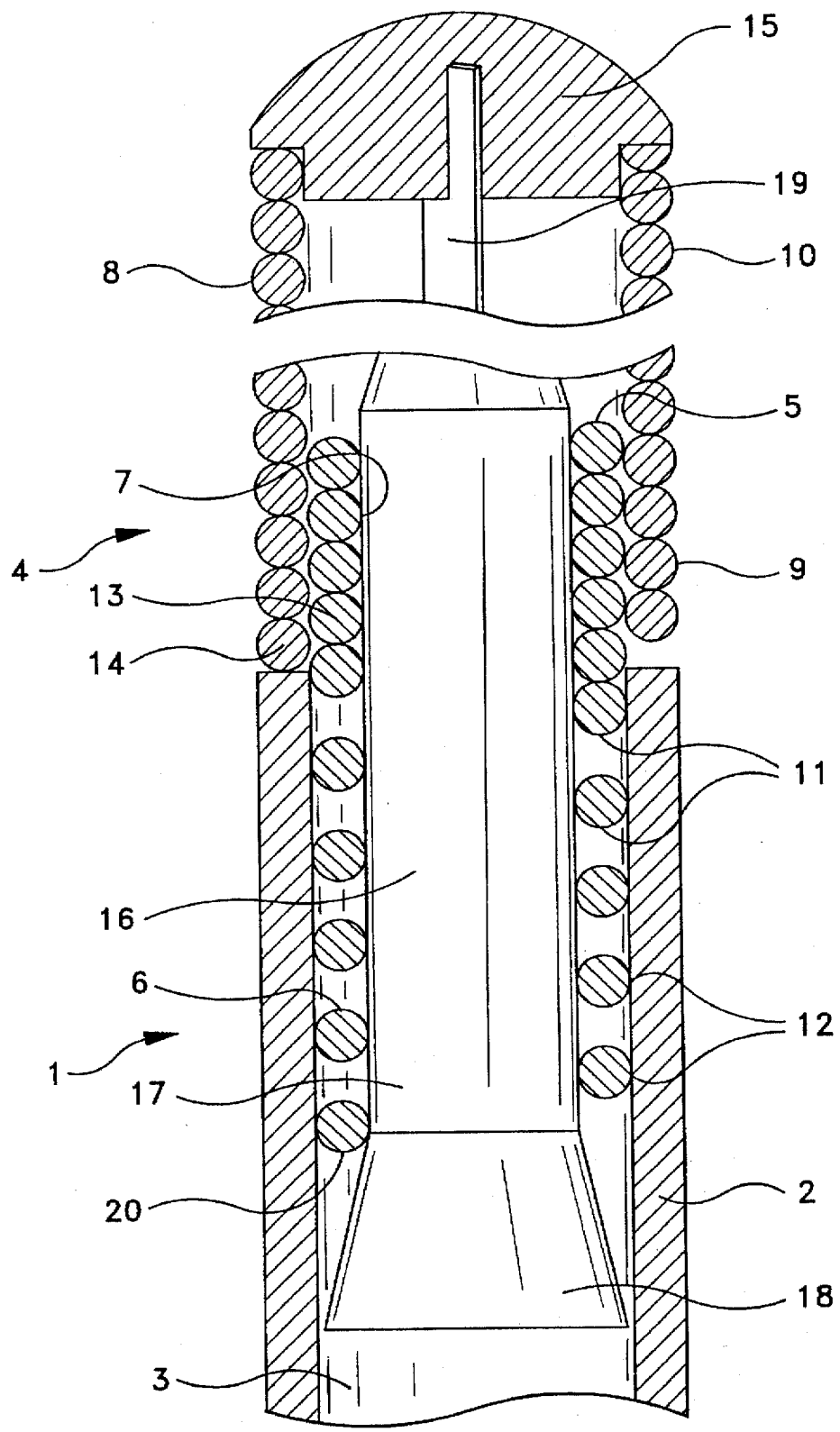
FIG. 1 is a cross sectional view of the distal portion of the guide wire.

The guide wire 1 comprises an elongated shaft 2 having a proximal portion (not shown) and a distal portion 3. As shown, this shaft is tubular.

Preferably, the shaft is made of an elastic nickel titanium alloy such as for instance Nitinol (Trade Name) or Tinel Alloy (Trade Name). Other materials are also possible, for example plastic materials.

A coaxial helical coil assembly 4 is arranged at the distal portion 3 of the shaft 2. This assembly 4 comprises a first coil 5 having a proximal portion 6 and a distal portion 7, and a second coil 8 having a proximal portion 9 and a distal portion 10 ending in a weld tip 15.

The proximal portion 6 of the first coil 5 comprises adjacent windings 11 which are spaced apart, and this proximal portion 6 is threadedly force fitted into the tubular distal portion 3 of shaft 2. Preferably, an adhesive (not shown) is injected between the windings 11.

The first coil 5 is made of a high density metal, preferably tungsten, in order to be highly radiopaque, and to create in the softer material of the distal portion 3 of shaft 2 a shape conforming way 12 in the form of a thread.

The second coil 8, also preferably made of a high density metal such as tungsten for radiopacity purposes, has its proximal portion 9 surrounding the distal portion 7 of first coil 5 the windings 13 of which are in threading engagement with the corresponding windings 14 of second coil 8. Preferably the proximal portion of second coil 8 abuts against the distal portion 3 of shaft 2 and this proximal portion of the second coil 8 is flush with the distal portion of shaft 2.

A cylindrical core 16, for instance of stainless steel, extends through the first coil 5, said core having preferably a proximal portion 17 in flush engagement with the first coil. The proximal end 18 of core 16 is flattened so that the resulting enlargement abuts longitudinally against the proximal end 20 of the coil 5. The core 16 tapers into a flattened straight and narrow distal portion 19 which terminates by welding into the tip 15.

Variants are available without departing from the scope of the invention. For instance, the shaft 1 may be only tubular at its distal portion 3; it may also be made of compound materials whereby only the distal portion of the shaft would be made of a nickel titanium alloy or of a plastic material. The adjacent windings 11 of the proximal portion 6 of first coil 5 may be close to one another. The second coil may be aligned with the first coil, whereby the windings of the proximal portion of the second coil could be screwed into the windings of the distal portion of the first coil or otherwise joined thereto. The proximal end 20 of the core member may have a circular shoulder instead of being flattened for longitudinal abutment with the proximal end 20 of the first coil 5.

I claim:

1. A guide wire comprising an elongated flexible shaft with a proximal portion and a distal portion, and a coaxial helical coil assembly at the distal portion of said shaft, said coaxial helical coil assembly comprising a first coil having a proximal portion and a distal portion, said first coil joined to the shaft, and a second coil having a proximal portion joined to the distal portion of the first coil and a distal portion terminating into a tip, wherein at least the distal portion of the shaft is tubular, and the proximal portion of the first coil is threadedly force fitted into the tubular distal portion of the shaft, whereby the first coil makes a thread way into the tubular distal portion of the shaft.

2. A guide wire according to claim 1, wherein the proximal portion of the first coil has adjacent windings which are spaced apart.

3. A guide wire according to claim 2, wherein an adhesive is sucked into the proximal portion of the first coil.

4. A guide wire according to claim 1, wherein the proximal portion of the second coil surrounds the distal portion of the first coil, and wherein the proximal portion of the second coil has windings in threading engagement with windings of the distal portion of the first coil.

5. A guide wire according to claim 4, wherein the proximal portion of the second coil abuts against the distal portion of shaft.

6. A guide wire according to claim 5, wherein the proximal portion of the second coil is flush with the distal portion of shaft.

7. A guide wire according to claim 1, further comprising core means extending through the first coil.

8. A guide wire according to claim 7, wherein said core means has a proximal portion in flush engagement with the first coil.

9. A guide wire according to claim 7, wherein said core means has a proximal end in longitudinal abutment against the proximal end of said first coil, and a distal portion terminating into the tip of the distal portion of the second coil.

10. A guide wire according to claim 1, wherein at least the tubular distal portion of the shaft is made of an elastic nickel titanium alloy.

11. A guide wire according to claim 1, wherein at least the tubular distal portion of the shaft is made of a plastic material.

12. A guide wire according to claim 1, wherein the first and second coils are made of high density metal.

13. A guide wire according to claim 12, wherein the first and second coils are made of tungsten.

14. A guidewire comprising:
    (a) a tube;
    (b) a core disposed at least partially within the tube and creating a space between a portion of the core and a portion of the tube;
    (c) a first coil having a proximal portion and a distal portion, the proximal portion disposed within the space and threadedly fixed to the tube;
    (d) a second coil having a proximal portion and a distal portion, the proximal portion coaxially joined to the distal portion of the first coil; and
    (e) a tip attached to the distal portion of the second coil.

15. The guidewire of claim 14 wherein the proximal portion of the first coil has adjacent windings which are spaced apart.

16. The guidewire of claim 15 further comprising adhesive dispersed between the windings.

17. The guidewire of claim 14 wherein the proximal portion of the second coil surrounds the distal portion of the first coil and the proximal portion of the second coil has windings in threaded engagement with windings of the distal portion of the first coil.

18. The guidewire of claim 14 wherein the core has a proximal portion in flush engagement with the first coil.

* * * * *